United States Patent [19]
Salpeter

[11] Patent Number: 5,230,863
[45] Date of Patent: Jul. 27, 1993

[54] METHOD OF CALIBRATING AN AUTOMATIC CHEMICAL ANALYZER

[75] Inventor: Jerome Salpeter, Yorktown, N.Y.

[73] Assignee: SI Industrial Instruments, Inc., Hawthorne, N.Y.

[21] Appl. No.: 816,706

[22] Filed: Jan. 2, 1992

Related U.S. Application Data

[63] Continuation-in-part of Ser. No. 204,689, Jun. 9, 1988, abandoned, which is a continuation-in-part of Ser. No. 76,066, Jul. 21, 1987, abandoned.

[51] Int. Cl.$^5$ ............................................. G01N 31/00
[52] U.S. Cl. ..................................... 422/67; 422/81; 422/82; 436/8; 436/52; 436/53; 356/408; 356/409; 356/410; 356/436; 250/252.1; 73/1 R
[58] Field of Search ............... 422/81, 82, 64, 65, 422/66, 67; 436/52, 53; 73/1 R; 356/408, 409, 410, 411, 414, 436; 250/252.1

[56] References Cited

U.S. PATENT DOCUMENTS

| | | | |
|---|---|---|---|
| 3,634,868 | 1/1972 | Pelavin et al. | 356/408 X |
| 3,960,497 | 6/1976 | Acord | 422/108 X |
| 3,970,392 | 7/1976 | Figueroa et al. | 356/409 X |
| 3,992,109 | 11/1976 | Bock | 436/52 X |
| 4,043,756 | 8/1977 | Sommervold | 422/81 X |
| 4,158,545 | 6/1979 | Yamashita et al. | 23/230 R |
| 4,313,735 | 2/1982 | Yamashita et al. | 422/67 X |
| 4,536,369 | 8/1985 | Sakurada et al. | 422/65 |
| 4,539,296 | 9/1985 | Manabe | 436/47 |
| 4,545,957 | 10/1985 | Vanhumbeeck et al. | 422/81 |
| 4,558,953 | 12/1985 | Yamada | 356/414 X |
| 4,678,755 | 7/1987 | Shinohara et al. | 436/43 |

Primary Examiner—James C. Housel
Assistant Examiner—Maureen M. Wallenhorst
Attorney, Agent, or Firm—Darby & Darby

[57] ABSTRACT

An automatic chemical analyzer includes containers for chemical reagents, a standard (full scale) solution and a baseline solution. An overflow sampler provides a test sample having a chemical concentration to be measured. Computer controlled valve means connect either the baseline solution, standard solution or test sample to an output tube, and a peristaltic pump couples the reagents and the liquid in the output tube to a chemical module where the chemical reaction takes place. The output of the chemical module is coupled to a flow cell in the form of a stream of liquid segments separated by air bubbles. Light at a selected optical frequency is passed directly through the flow cell to a photodetector the output of which is converted to digital form by a computer which stores baseline and full scale values corresponding to the color values of the liquids in the baseline and standard containers. To ensure accurate calibration, baseline values are determined separately for baseline solutions without color reagent and baseline solutions with color reagent.

2 Claims, 2 Drawing Sheets

METHOD OF CALIBRATING AN AUTOMATIC CHEMICAL ANALYZER

This is a continuation-in-part of U.S. patent application Ser. No. 07/204,689 filed Jun. 9, 1988, now abandoned, which is a continuation-in-part of U.S. patent application Ser. No. 7,076,066, filed Jul. 21, 1987, now abandoned, and entitled "Automatic Chemical Analyzer".

This invention relates to apparatus for measuring the concentration of chemicals in fluids. More particularly, this invention relates to an improved calibration technique for a colorimetric analyzer capable of continuously measuring the concentration of preselected chemicals in a flow of liquid.

BACKGROUND OF THE INVENTION

In power plants, it is necessary to monitor the concentration of soluble silica compounds in the water fed to and in the boilers. Excessive amounts of such compounds (referred to hereinafter as "silica") can cause coating of the turbine blades which requires costly maintenance on a periodic basis. Typically, silica concentrations in excess of 20 parts per billion (ppb) are considered excessive.

Analyzers have been sold for continuously monitoring the concentration of silica and other chemical compositions in water and other fluids. One such device was manufactured and sold by Orion Scientific Instruments of Hawthorne, N.Y. as the Orion Model 1830 Silica Analyzer (hereinafter referred to as the Orion analyzer).

The Orion analyzer coupled a sample of water to be analyzed to a chemical cartridge where known reagents were added and mixed in proper sequence to yield a heteropoly blue complex, the intensity of which was proportional to the silica concentration. The heteropoly blue complex was then pumped to a flow cell positioned in a colorimeter of the type shown in U.S. Pat. No. 4,273,449 of Schmid entitled "Radiation Measuring Apparatus".

This colorimeter directed light through the flow cell and through a reference path so that adjustments for changes in the optical signals could be accommodated. In accordance with known procedures, a baseline value (corresponding to a zero silica content) and a full scale value could be entered into storage in a microprocessor which would then calculate a calibration curve. These data entries were made manually by the operator who would select the switching of a baseline solution and a standard solution to the chemical cartridge and flow cell for the necessary measurements. After the analyzer had been calibrated the operator would then connect the sample to the analyzer and the analyzer would then be able to compare the colorimetric values, after the appropriate reactions, with the calibration curve in the memory of the microprocessor.

The Orion analyzer had a number of drawbacks. In the first place, the procedure was not automatic and a fairly high level of skill was required to prepare and calibrate the analyzer for the sample measurements. For example, the reflecting surfaces of a prism used to divide the beam between the reference cell and flow cell paths had to be initially adjusted so that the two detectors produced essentially the same output at the start. This was necessary because the detectors were part of a ratio system. Errors in the calibration and setup procedures would be reflected in the readings of the analyzer while monitoring the sample to be tested.

Furthermore, the colorimetric system used in the Orion analyzer and as shown in the '449 patent required a flow cell having a relatively long path length to provide adequate sensitivities for very low concentrations. This was caused in part by the need to use a beam divider to separate the light into measurement and reference paths. Reflections caused by the beam divider result in a loss of light energy (i.e., the beam divider is less efficient than a "straight through system"). Thus, when low signal levels or relatively low "delta" signals are processed, the signal-to-noise level becomes a problem in detecting low concentration levels. The beam divider system thus requires the use of a long flow cell light path to compensate for a very low energy difference between the baseline solution and the absorption where the concentration of the parameter being measured is very low. However, increasing the length of the flow cell increases the tendency of air bubbles to collect in the cell. This gives rise to a serious problem. The stream within the analyzer comprise pockets of fluid separated by air bubbles. These air bubbles are discarded before the fluid enters the flow cell. However, the presence of entrapped air bubbles in the flow cell of the colorimetric analyzer, even if microscopic in size, affects the transmission of light through the cell and, therefore, is likely to cause false readings and noisy recordings. The type of flow cell commonly used today for continuous colorimetric analysis does not lend itself to reliable venting of all air within the samples under test.

OBJECTS OF THE INVENTION

In practice, the reagents may be used for a long time, e.g., one month, during which time the chemical sensitivity (or insensitivity) of the reagents is subject to change. This change in chemical sensitivity may cause "drift" of the base line calibration which can have a significant effect on measurements at very low concentration levels.

Accordingly, the principal object of this invention is to provide a base line calibration system for an automatic chemical analyzer wherein calibration is adjusted on a regular periodic basis to compensate for changes in the baseline due to electronic and/or chemical changes in the system.

SUMMARY OF THE INVENTION

Briefly, in accordance with the invention, a computer controlled valving arrangement couples either the solution to be tested, a baseline solution or a standard (full scale) solution to a chemical cartridge through a pumping mechanism which also feeds the desired reagents to the cartridge. After the chemical reaction takes place in the cartridge, the liquid in the cartridge is fed to a flow cell which includes a chamber having walls through which the desired light source is passed to a detector such as a photodiode. In accordance with the invention, the baseline solution and standard (full scale) solutions are first passed through the flow cell automatically and the values of the light intensities for each stored in memory in the computer. The computer calculates the calibration curve from these values so that thereafter, as the sample is tested, the voltages detected can be correlated within the computer to specific chemical concentrations. To establish an exact baseline value, a baseline solution is provided including all of the chemical reagents with the exception of the color reagent. During calibration the baseline solution without the color reagent is passed to the flow cell and a baseline value with no color reagent present (i.e., corresponding to no detectable silica) established. On a periodic basis (for example, every eight hours) a baseline value with color reagent present is also calculated and compared to the prior day's measurement automatically. If a change is measured, either because of electronic or chemical reasons, an appropriate adjustment of the calibration curve is made.

THE DRAWINGS

DETAILED DESCRIPTION

An analyzer, in accordance with the invention, can be used in any continuous process wherein reagents are mixed with a continuous stream of a liquid to be tested. For purposes of explanation only, the invention is described as it would be used to test for the presence of soluble silicates (silica) for example in power plants where the presence of such silicates is undesirable because of their tendency to coat the turbine blades.

In a typical industrial use, it may be desirable to maintain the level of silica at 20 ppb. In such a case the full scale value typically may be in the order of 100 ppb. The principals of the invention are not restricted to any particular type of chemical analysis nor, of course, to a particular range. For purposes of explanation only, the preferred embodiment described as part of an automated continuous system for measuring the amount of silicate present in a continuous flow of water (e.g., from a power plant).

Figure 1:
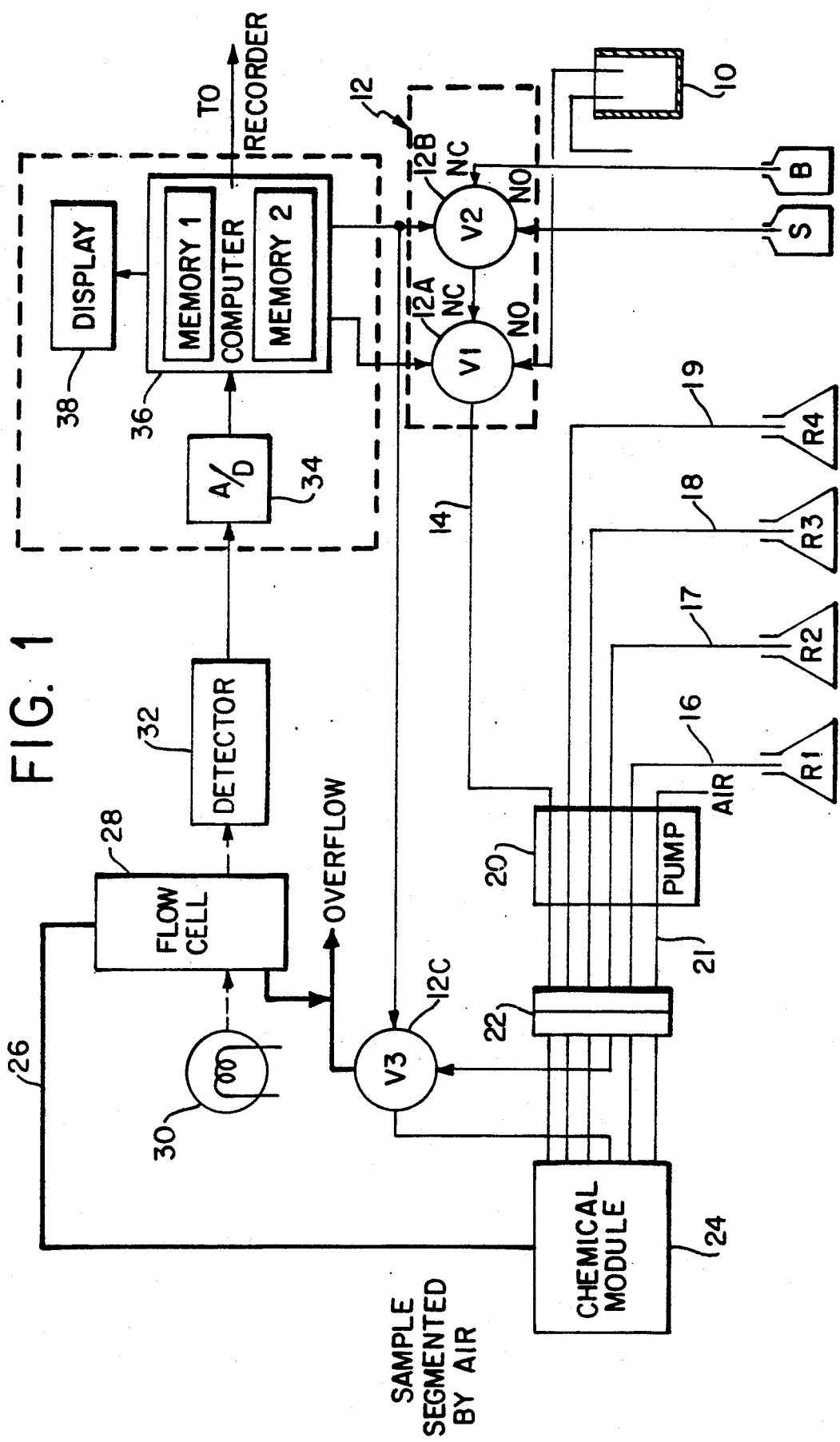
FIG. 1 is a diagrammatic block diagram showing the mechanical and electrical components of a preferred embodiment of the invention.

In FIG. 1 the fluid flow is represented by heavy lines and the electrical connections by lighter lines.

The typical reaction for detecting silicates involves four reagents: sulfuric acid, ammonium molybdate, oxalic acid and ascorbic acid. These reagents are held in four containers R1, R2, R3 and R4, respectively. The standard solution is held within a container S and the baseline solution in a container B. The water to be monitored is filtered to remove particulate matter and fed to an overflow sampler 10 which may be of a known construction and provides a continuous stream of water to the analyzer.

The liquid outputs from the overflow sampler 10, the standard container S and the baseline container B are coupled to solenoid controlled valves 12A and 12B which, as explained below, connect one of these three containers to an output tube 14 at appropriate times during the analyzer cycle. Output tube 14 along with the tubes 16-19 from reagent containers R1-R4, respectively are pressed beneath the roller of a peristaltic pump 20 through a disconnect device 22 to a chemical module where the chemical reaction takes place.

Peristaltic pumps are known devices for providing pockets of fluid. Pump 20, for example, may have the construction shown in U.S. Pat. No. 4,233,001 of Schmid entitled "Peristaltic Pump." As shown in the '001 patent, the rotation of a roller occludes the tubes which pass beneath it creating a pressure differential which results in a steady pumping action causing pockets of fluid to pass through the tubes. In the preferred embodiment, tubes 14 and 16-19 are color coded to identify the reagent or solution, and the tubes are held in a predetermined spaced relationship by means of collars or the like (not shown). An air tube 21 open to atmosphere provides the air that is pumped into the line to separate the liquid flow into a multiplicity of segments. The disconnector 22 also is a commercially available device which provides a convenient means for connecting the chemical module 24 to the tubes 14, 16-19 and 21.

Chemical module 24 also may be of known construction. The module comprises an insulated heater housing adapted to receive a removable sealed chemistry cartridge (not shown). The chemical cartridge is sealed to prevent breakage and to provide for better temperature control. The purpose of the cartridge is to direct the chemistry, i.e., to add the various reagents from tubes 16-19 at the proper time, to mix the reagents and the sample or solutions from valve 12A and 12B, and to provide the necessary delays for the reactions to take place. Such devices are known including, in particular, devices for directing the chemistry required to detect the presence of silica in power plants. The output from the cartridge passes through a tube 26 to a flow cell 28 in the form of a segmented stream with each segment separated by small air bubbles pumped through tube 21.

The system as described to this point is known. As the reagent and samples are passed through the chemical cartridge within the module 24, a chemical reaction takes place. The sample is first acidified with sulfuric acid and then reacted with ammonium molybdate to yield a silicomolybdate complex. The oxalic acid breaks up the phosphomolybdate complex but does not affect the silicomolybdate complex. Ascorbic acid then reduces the silica molybdate complex to a heteropoly blue complex which is blue-green in color. As is well-known, the absorbance (transmittance) of the heteropoly blue complex can be measured by passing light at a wavelength at 820 nanometers (nm) or 660 nm through the liquid and detecting the amount of light passing through the sample. The detector output provides an indication of the silica content in the sample. This determination is made in accordance with the invention as described below.

As explained below, in accordance with one aspect of the invention, when the baseline solution B flows into the system, the ammonium molybdate (i.e., reagent R2) is by-passed from flow cell 28. For this purpose, a third solenoid controlled valve 12C is connected between disconnector 22 and chemical module 24 in the line 17 containing ammonium molybdate. Valve 12C normally couples line 17 to chemical module 24. When activated, it redirects line 17 to overflow (waste). Valves 12B and 12C may be operated together so that when valve 12B connects the baseline solution to valve V1 (and line 14 when valve 12A is activated), line 17 containing the ammonium molybdate is by-passed by valve 12C to overflow. Valve 12B may also be operated alone so that the baseline solution and color reagent in container R2 can be passed to flow cell 28 to determine a true blank as explained below.

A preferred embodiment of the flow cell 28 is described below with respect to FIGS. 2-4. One function of the flow cell is to debubble the output from the chemical module in tube 26 since the presence of bubbles in the flow cell can lead to false readings. The flow cell also must prevent the foam produced by any wetting agents in the solution from affecting any readings. Such wetting agents are used to minimize back pressure due to the relatively narrow bore tubing used in the preferred embodiment and, typically, are added to the reagents. In addition, the flow cell provides a constant level device from the constantly flowing stream of water.

A light source shown at 30 directs light at the desired wavelength (e.g., 820 nm) through the measuring chamber of the flow cell 28 where it is detected by detector 32. Detector 32 produces a voltage output which is proportional to the amount of light passing through the flow cell (and, therefore, the quantity of silica in solution).

The analog voltage from detector 32 is connected to an analog to digital converter 34 which couples its digital output to a computer 36, e.g., a microprocessor. Computer 36 is programmed, as explained below, to provide an output indicative of the quantity of silicate in the sample. This output may be displayed on a display device 38 and it may also be transmitted to a recorder to maintain a permanent record. In addition, the computer 36 provides timing signals to the solenoid operated valves 12A, 12B and 12C to determine which of the standard, baseline or sample solutions is to be fed into tube 14 and valve 12C to by-pass the ammonium molybdate (reagent R2) to overflow.

The invention provides a completely automatic system for analyzing the sample. To do this, it is necessary to set up a reference within the computer 36 so that the measured values of light absorbance can be compared to the reference values to determine the silica content. The baseline solution in container B is a solution made as free of silica as possible (e.g., 0 ppb). The standard solution in container S is the full scale value of the analyzer and it will be set by the operator. For example, if it is desired to maintain a silica content of less than 20 ppb, a standard solution may be prepared in which the silica concentration is 100 ppb. As now explained, during the initializing process, the computer 36 stores in memory the values of the output signals from detector 32 corresponding to both the baseline and standard solutions. Since the relationship of light absorbance in flow cell 28 to silica concentration is linear, the output of the detector 32 can be compared with the values stored in the computer 36 for the baseline and standard solutions and the silica concentration calculated and displayed.

The operation of the system is as follows. The reagent bottles R1-R4 and the standard and baseline containers S and B are filled with the proper solutions. The overflow sample 10 is coupled to a port in the plant so that the sample to be measured is available at the input to the valve 12A. The user then pushes a button to start the operation. Immediately, computer 36 causes valves 12A and 12B to connect the baseline container B to the tube 14 and valve 12C to by-pass the ammonium molybdate (reagent R2) to overflow. Simultaneously, pump 20 is turned onto high speed for the purpose of pumping the reagents and baseline solution into the analyzer as quickly as possible. For example, pump 20 may normally operate at 3.7 rpm; at high speed, it may operate at 12 rpm.

After a period of six minutes, the computer causes the pump 20 to operate at normal speed for sixteen minutes. At the end of this initial period (twenty-two minutes in this example) the baseline solution fully occupies the flow cell 28 so that the analyzer is measuring the light through the flow cell when the silica concentration is zero. Thus, the output of detector 32 represents the light intensity where the silica in solution is zero. Because ammonium molybdate is not in the chemical module during the baseline measuring period, no change in color is possible and the output of detector 32 therefore exactly represents zero silica. This value is converted to digital form and stored in memory M1 within the computer 36.

The computer then actuates the solenoid operated valves 12A, 12B and 12C to couple the standard solution in container S to the tube 14, reconnect reagent R2 (ammonium molybdate to chemical module 24, and at the same time cause pump 20 to operate at high speed. This high speed operation continues until the standard solution reaches the chemical module 24, for example, three minutes. For any given system, of course, this time interval is known and can be programmed into the computer. When the standard solution is in the chemical module 24, the computer returns pump 20 to normal speed. At normal speed, in the preferred embodiment, it may take about sixteen more minutes to replace the baseline solution in the flow cell 28 with the standard solution flowing from the chemical module 24.

When this time interval has passed, the intensity of the light passed through the flow cell 28 represents the silica content of the known standard. Accordingly, this value is sensed by the detector 32, converted to digital form in converter 34 and stored in memory M2.

Knowing the values for the baseline and standard solutions, the computer establishes a calibration curve in accordance with known procedures. For example, if the output of detector 32 is at a certain value at 0 ppb and a second value at 100 ppb and if there is a linear relationship between detector output and silica content (or if the shape of the curve is otherwise known) then whatever the value of the output of detector 32, the computer 36 can calculate the silica content for display and/or recording or other purposes.

In accordance with the invention, a third calibration point is measured and stored in computer 36. This third calibration point, referred to herein as the "true blank", is determined by adding the color reagent in container R2 to the baseline solution in the container B. For this purpose the computer actuates only the valves 12A and 12B (but not valve 12C) for essentially the same time sequences described above, causing the baseline solution and color reagent to fully occupy the flow cell 28 after the initialization period. Since color reagent is present, if there is any silica present in the reagents, it will be sensed at the output of detector 32 and the value, in digital form, stored in memory M1 within computer 36.

After the calibration curve has been stored in the computer, the computer then signals the solenoid control valve 12A to couple the overflow sampler 10 to the tube 14. In this condition, the analyzer continuously analyzes the flow of sample through the overflow sampler 10 for silica content.

The calibration technique, wherein a baseline without color reagent and a baseline with color reagent are determined, permits accurate measurements at extremely low levels of silica concentration, for example less than three parts per billion. Because of the determination of the true blank, the content of any contamination within the reagents is known. Since the absolute zero concentration point is also known, i.e., the baseline without color reagent, the system is therefore capable of making measurements below the contamination level of the reagents. This was not possible with the prior systems wherein only a single baseline value was determined either with the color reagent or without the color reagent.

Periodically, for example every eight or twelve hours, the computer 36 will cause the solenoid control valves 12A and 12B to introduce the baseline solution in container B and color reagent in R2 into the system through tube 14. When this occurs, there is again high speed operation for about six minutes followed by sixteen minutes at normal speed so that a new true blank value can be determined.

The true blank value is then compared with the previously measured true blank value. If it has changed, the calibration curve is "shifted" as explained below to compensate for any drift introduced into the system. Such drift can be caused by temperature changes, electronic drift in the equipment, and degradation of the reagents which may decrease sensitivity of the system. If only a baseline calibration without the color reagent was made, the change in drift due to the chemical changes of the reagents would not be accommodated in the calibration process. This can be a significant factor, particularly at extremely low concentration levels.

The calibration curve is "shifted" to accommodate any detected drift as follows. Since the shape of the calibration curve is known, when the absolute baseline (without color reagent) and full scale standard are measured, the calibration curve can be determined so that absorbance can be correlated to silica concentration. Because the silica concentration of the true blank is also measured in accordance with the invention, if a subsequent measurement (for example, eight to twelve hours later) reflects a change in absorbance of the true blank, the calibration curve can be "shifted" by the computer such that the concentration of the true blank as measured on the calibration curve is returned to the previously measured value. The change in absorbance may be caused by any of the above measured factors, including possibly a chemical change in reagent sensitivity which is not detectable if one measures only the baseline without the color reagent.

At longer periodic intervals, both the baseline and standard or full scale values are calculated and stored in memory. For example, every forty-eight hours the entire process may be recycled.

Figure 2:
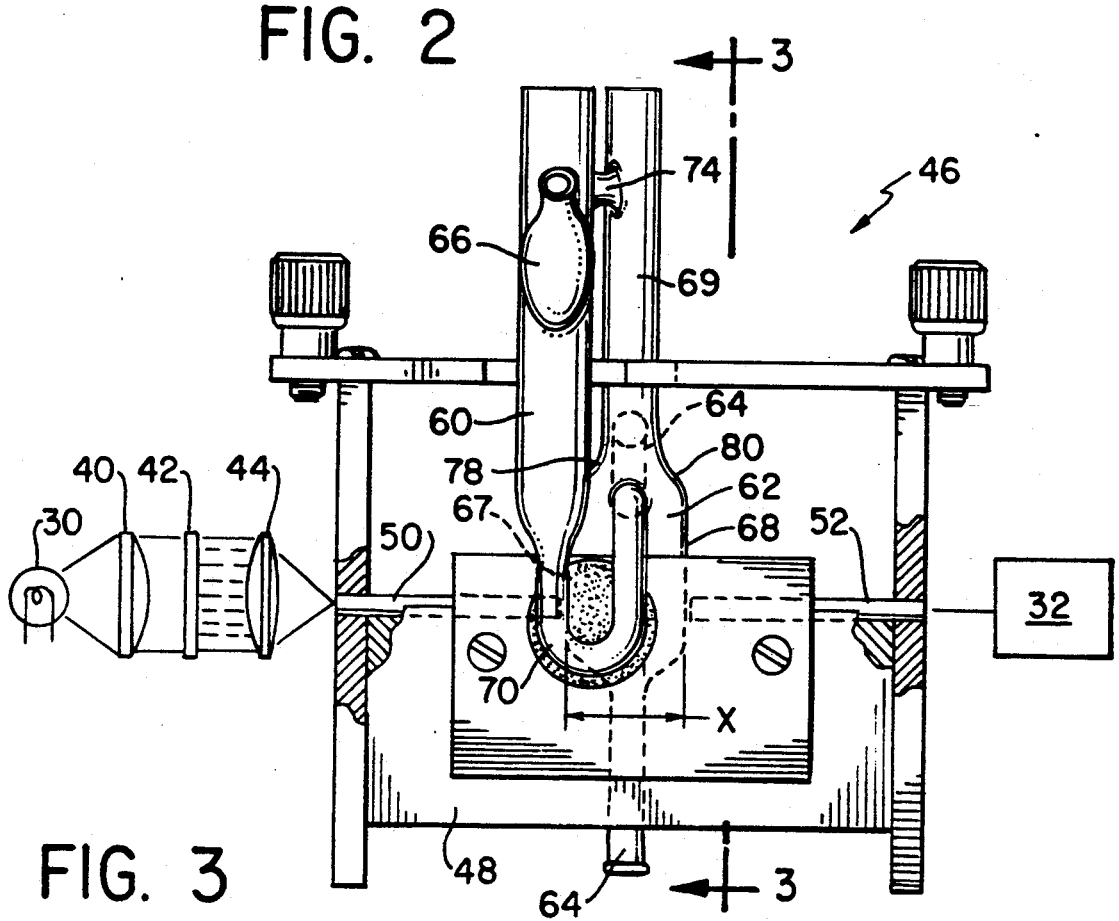
FIG. 2 illustrates diagrammatically the optical train of a colorimeter in accordance with a preferred embodiment of the invention in conjunction with a front plan view of a flow cell and the mechanical structure used to support the flow cell.

The optical train according to a preferred embodiment of the invention is shown in FIG. 2. The light output from source lamp 30 is coupled through a collimating lens 40, an interference filter 42 and a condenser lens 44. The filter 42 removes all but the desired wavelength, 820 nm in this example. Reasonably collimated light is necessary since the interference filter can be made efficiently for only a restricted angle of incidence.

The flow cell 28 is held in a support assembly 46 which includes a firmly supported bracket 48 adapted to securely hold light pipes 50 and 52 in suitable V grooves (not numbered). The light pipes 50 and 52, arranged on opposite sides of the flow cell 28, direct the filtered light from condenser lens 44 through the liquid within the flow cell to detector 32, typically a photodiode.

Condenser lens 44 functions as a decollimator and should have a high numerical aperture to minimize energy losses due to diffusion. The condenser lens focuses the available light energy onto the entrance face of the light pipe 50. The light pipes 50 and 52 are able to direct the light with minimal losses to the active portion of the cell and then direct the attenuated light out to the active photodetector surface.

In operation, light enters the front face of the entrance light pipe 50 of the flow cell and is directed onto the entrance surface of the flow cell proper. The colored sample absorbs a fixed portion of the nominally-monochromatic light. The attenuated light is then directed out through the exit light pipe 52.

All the light from the exit face of the flow cell strikes the active surface of the solid-state photodetector 32. The detector converts impinged light from 340 to 900 nm into a corresponding electrical signal which is processed in the electronics package. The optical train and detectors respond accurately in the typically linear Beer-Lambert relationship between absorbance and concentration.

Energy losses in the optical system are minimized by careful design and selection of optical components. Less energy is lost with the use of a single large-diameter, high through-put narrow-band optical filter than a conventional, small-diameter dual filter system.

The flow cell 26 is an important part of the invention and while it is not novel per se, similar devices having been used in other colorimetry systems, it provides special benefits in the type of analyzer to which the invention pertains.

Figure 3:
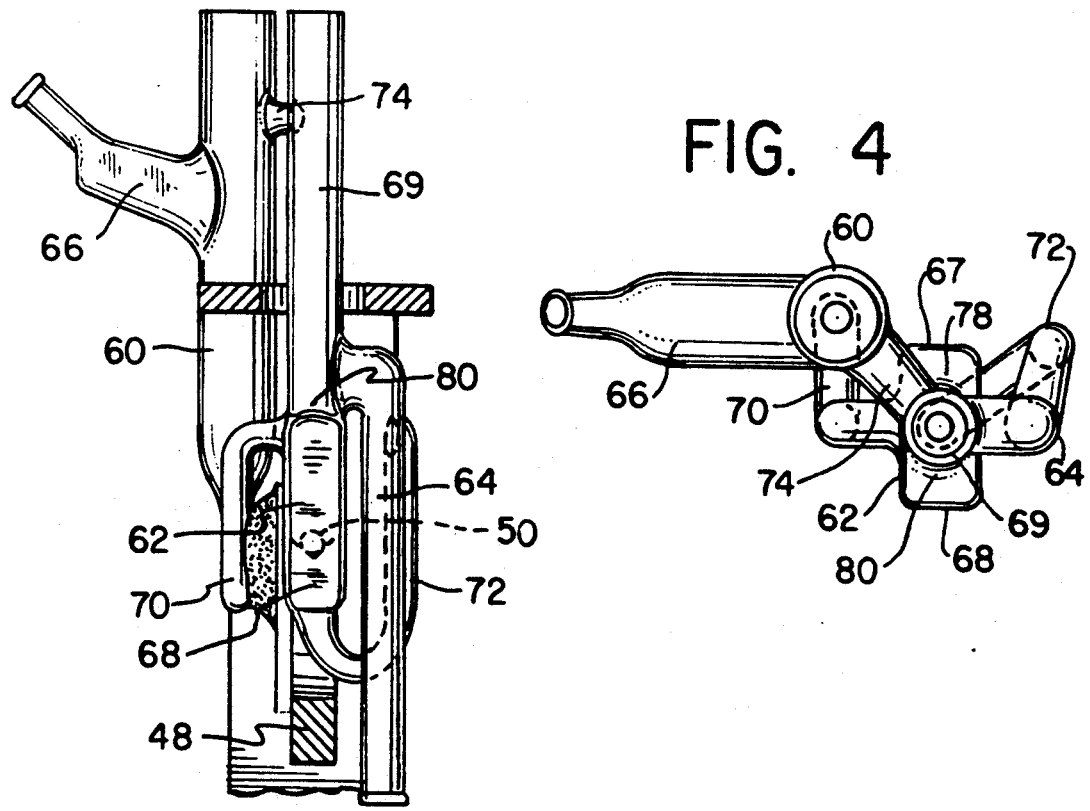
FIG. 3 is a front view of the flow cell.
Figure 4:
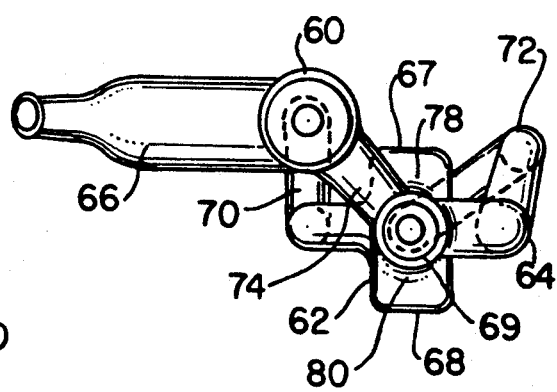
FIG. 4 is a top view of the flow cell.

As shown in FIGS. 2–4, the flow cell which may be made of glass includes a reservoir 60, a measuring chamber 62 and an overflow pipe 64. An inlet pipe 66 introduces the liquid to be tested into the vertical reservoir 60. The measuring chamber 62 is essentially vertical in cross-section and as shown in FIG. 3 includes opposing sides 67 and 68 and a venting tube 69 open to atmosphere. The light from lamp 30 passes through the sides 67 and 68 which are polished to minimize reflections and optical losses. The liquid within reservoir 60 is fed through a U-shaped tube 70 into the upper portion of the measuring chamber 62 of the flow cell (see FIG. 2). The liquid from the measuring chamber 62 is coupled to the overflow pipe 64 by means of a similarly U-shaped tube 72. This particular configuration shown in FIGS. 2–4 is used in the preferred embodiment of the invention because it is adapted to be conveniently retained within the existing support carriage of the Orion analyzer but, as now explained, the only critical structural aspects of the flow cell reside in the shape of the measuring chamber 62 and its relation to the venting tube 69.

As is well-known from the Beer-Lambert formula, light absorbance (transmissivity) is dependent upon the length of the light path through the flow cell or, in this case, the distance between the surfaces 67 and 68 as represented by the dimension X in FIG. 2. For very low chemical concentrations, the dimension X should be as large as possible. However, because of the need to vent the system of air bubbles among other things, there is a practical limit on the length of dimension X.

The air bubbles that create segmented flow to the flow cell 28 permit sample-to-sample discretion thereby enhancing the response time by avoiding averaging. Also, the air bubbles tend to scrub the walls of the glass tubes and generally improve mixing which are desirable features. As mentioned above, the air bubbles are introduced into the liquid stream by means of the tube 21 which is vented to atmosphere.

Also as indicated above, a principal problem with the Orion analyzer was its inability to totally and reliably void the system of air after the air bubbles had been introduced into line 26. The construction of the flow cell illustrated in FIGS. 2–4 is far superior to the flow cell used in the Orion analyzer and shown in the '449 patent because the measuring chamber 62 is vented directly to atmosphere by the tube 69. However, the fact that the measuring chamber is vented also creates problems since if the diameter of the venting tube 69 is too large, the flow cell will combine the discrete samples (previously separated by air bubbles) which causes averaging and thus tends to reduce response time. On the other hand, if the size of the vent 69 is too small, the surfaces 67 and 68 of measuring chamber 62 extend outside the walls of the venting tube 69 creating shoulders 78 and 80 where air bubbles tend to collect. If the differential in size is small, the shoulders 78 and 80 can be severely sloped as shown in FIG. 2 to minimize this problem but if the dimension X is large, then it is impossible to simultaneously avoid the problem of averaging and the problem of accumulating air bubbles. Through experiments, it has been discovered that the maximum length of the dimension X is approximately 30 millimeters. At this dimension, the maximum size of the venting tube 69 which will avoid averaging of samples also will allow virtually complete venting of all air within the liquid in the flow cell.

Flow cells with a dimension X of less than 30 mm of course can be used and, in fact, are preferred where concentrations substantially higher than 20 ppb are detected.

What is claimed is:

1. A method of calibrating a chemical analyzer of the type in which light at a predetermined frequency is passed through a flow cell containing a sample with an analyte to be measured, wherein a color reagent is added to the sample to cause a color concentration in the sample which is indicative of the concentration of the analyte to be measured with in said sample, and wherein the intensity of the light passing through the flow cell is compared to a previously calibrated curve of light intensity versus concentration to provide a measure of the concentration of said analyte in said sample, comprising passing a baseline solution to said flow cell, said baseline solution being devoid of color reagent and said analyte, measuring the intensity of said light passed through said baseline solution in said flow cell and storing the value of said intensity as a baseline value, passing a standard solution to said flow cell, said standard solution containing a color reagent and a known concentration of the analyte to be measured, measuring the intensity of said light passed through said standard solution in said flow cell and storing the value of said intensity as a full scale standard value, establishing a calibration curve based on said baseline value and said full scale standard value, passing said baseline solution and a color reagent to said flow cell, measuring the intensity of said light passed through said baseline solution and color reagent to establish a true blank value, and adjusting said calibration curve based on said true blank value to compensate for changes in the sensitivity of the analyzer or the color reagent.

2. A method of calibrating a chemical analyzer according to claim 1, further including the steps of measuring true blank values on a periodic basis and adjusting the calibration curve depending on the difference between a currently measured true blank value and a previously measured true blank value.

* * * * *